(12) United States Patent
Mueller, Jr. et al.

(10) Patent No.: US 7,704,226 B2
(45) Date of Patent: Apr. 27, 2010

(54) EXTERNAL INFUSION DEVICE WITH PROGRAMMABLE CAPABILITIES TO TIME-SHIFT BASAL INSULIN AND METHOD OF USING THE SAME

(75) Inventors: John C. Mueller, Jr., Simi Valley, CA (US); Carol L. Davis, Agua Dulce, CA (US); Paul H. Kovelman, Simi Valley, CA (US); Mike Charles Vallet Tolle, Van Nuys, CA (US); Gary L. Williams, Gardena, CA (US); Linda I. Torres, Moorpark, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 883 days.

(21) Appl. No.: 11/282,453

(22) Filed: Nov. 17, 2005

(65) Prior Publication Data
US 2007/0112298 A1    May 17, 2007

(51) Int. Cl.
*A61M 5/172*    (2006.01)
(52) U.S. Cl. ....................................................... 604/65
(58) Field of Classification Search .................... 604/65, 604/66, 891.1
See application file for complete search history.

(56) References Cited

U.S. PATENT DOCUMENTS

| | | | | |
|---|---|---|---|---|
| 5,582,593 | A * | 12/1996 | Hultman | ........................ 604/65 |
| 6,554,798 | B1 | 4/2003 | Mann et al. | |
| 2003/0055406 | A1 | 3/2003 | Lebel et al. | |
| 2003/0114836 | A1 | 6/2003 | Estes et al. | |
| 2003/0160683 | A1 | 8/2003 | Blomquist | |
| 2003/0212379 | A1 | 11/2003 | Bylund et al. | |
| 2004/0068230 | A1 * | 4/2004 | Estes et al. | ................... 604/154 |
| 2005/0038332 | A1 * | 2/2005 | Saidara et al. | ............... 600/347 |
| 2005/0065464 | A1 * | 3/2005 | Talbot et al. | ................... 604/66 |
| 2005/0171513 | A1 * | 8/2005 | Mann et al. | ............... 604/890.1 |
| 2005/0240092 | A1 * | 10/2005 | Shah et al. | ................... 600/365 |
| 2006/0173406 | A1 * | 8/2006 | Hayes et al. | ................... 604/67 |
| 2007/0016170 | A1 * | 1/2007 | Kovelman | ................ 604/890.1 |
| 2007/0060870 | A1 * | 3/2007 | Tolle et al. | ..................... 604/65 |

(Continued)

FOREIGN PATENT DOCUMENTS

| WO | 00/10628 A2 | 3/2000 |
|---|---|---|
| WO | 00/74753 A1 | 12/2000 |

OTHER PUBLICATIONS

International Search Report for PCT/US2006/044050.
Walsh, John, P.A., C.D.E., "Changes in Diabetes Care A History of Insulin & Pumps Past, Present, and Future", Presentation, Sep. 2004.

*Primary Examiner*—Nicholas D Lucchesi
*Assistant Examiner*—Aarti B Berdichevsky

(57) ABSTRACT

An external infusion device for delivering insulin from a reservoir into a body of a user includes the capability to deliver time-shifted basal insulin. The external infusion device includes at least one drive mechanism operatively couplable to the reservoir to deliver insulin into the body of the user, at least one processor to control the external infusion device, at least one power supply, at least one display device operatively coupled to the processor to provide visual information to the user, at least one input device operatively coupled to the processor to allow the user to command the processor, and a housing. Time-shifting of basal insulin occurs when a portion of basal insulin is added to a bolus, to a current basal rate, or to a bolus and a current basal rate.

62 Claims, 5 Drawing Sheets

U.S. PATENT DOCUMENTS

2007/0142822 A1* 6/2007 Remde .................... 604/890.1
2007/0244383 A1* 10/2007 Talbot et al. ................ 600/365
2008/0033357 A1* 2/2008 Mann et al. ................. 604/131
2008/0064943 A1* 3/2008 Talbot et al. ................ 600/365

* cited by examiner

EXTERNAL INFUSION DEVICE WITH PROGRAMMABLE CAPABILITIES TO TIME-SHIFT BASAL INSULIN AND METHOD OF USING THE SAME

FIELD OF THE INVENTION

Embodiments of the invention relate to infusion devices and, more particularly, to infusion devices with programmable capabilities to time-shift basal insulin.

BACKGROUND OF THE INVENTION

Diabetes is a disease in which the body does not produce or properly use insulin. Approximately 13 million people in the United States have been diagnosed with some form of diabetes. Type 1 diabetes results from the body's failure to produce insulin. Type 2 diabetes results from insulin resistance in which the body fails to properly use insulin. To effectively manage the disease, diabetics must closely monitor and manage their blood glucose levels through exercise, diet and medication. In particular, both Type 1 and Type 2 diabetics rely on insulin delivery to control their diabetes. Traditionally, insulin has been injected with a syringe multiple times during the day, usually self-administered by the diabetic. In recent years, external infusion pump therapy has been increasing, especially for delivering insulin to diabetics using devices worn on a belt, in a pocket, or the like, with the insulin delivered from a reservoir via a catheter with a percutaneous needle or cannula placed in the subcutaneous tissue.

External infusion devices allow Type 1 and Type 2 diabetics to better manage and control their diabetes. The external infusion device is intended to be used continuously and delivers insulin twenty-four hours a day according to a programmed plan unique to each pump wearer. A small amount of insulin, or a basal rate, is given continually. This insulin keeps the user's blood glucose levels in the desired range between meals and over night. When food is eaten, the user programs the external infusion device to deliver a bolus of insulin matched to the amount of food that will be consumed. The user determines how much insulin will be given based on factors including insulin sensitivity, insulin duration, insulin-on-board, and the like. In many instances, external infusion devices include a processor that assists the user in making therapy decisions based on information provided by the user including blood glucose levels, carbohydrate intake, and/or information from the external infusion device. Exemplary devices are described in U.S. Pat. No. 6,554,798 issued on Apr. 29, 2003 to Mann et al., and entitled "External Infusion Device With Remote Programming, Bolus Estimator And/Or Vibration Alarm Capabilities," which is specifically incorporated by reference herein.

SUMMARY OF THE DISCLOSURE

According to an embodiment of the invention, an external infusion device delivers insulin from a reservoir into a body of a user. The external infusion device further includes at least one drive mechanism operatively couplable to the reservoir to deliver insulin into the body of the user, at least one processor to control the external infusion device, at least one power supply, at least one display device operatively coupled to the at least one processor to provide visual information to the user, at least one input device operatively coupled to the at least one processor to allow the user to command the at least one processor, and a housing. The external infusion device also includes the capability to deliver time-shifted basal insulin. In additional embodiments, the time-shifted basal insulin may be added to at least one bolus. In other embodiments, the time-shifted basal insulin may be added to a current basal rate.

In particular embodiments, the amount of time-shifted basal insulin to be delivered is selected by the user. In alternative embodiments, the amount of time-shifted basal insulin to be delivered is selected by the at least one processor. In still additional embodiments, the amount of time-shifted basal insulin to be delivered is based on externally supplied values including insulin action, insulin sensitivity, insulin-on-board, basal-on-board, anticipated carbohydrate intake, carbohydrate ratio, glycemic index values, blood glucose levels, and/or target blood glucose values.

In yet other embodiments, the at least one processor includes at least one customizable bolus delivery profile including different percentages of a square wave bolus, a dual wave bolus, a normal bolus, a meal bolus, and/or a time-shifted basal insulin bolus. In alternative embodiments, the amount of time-shifted basal insulin to be delivered is based on a percentage of the user's current basal rate. In particular embodiments, the user selects the percentage of a current basal rate to add and, in other embodiments, the at least one processor selects the percentage of a current basal rate to add. In still additional embodiments, the percentage of a current basal rate is based on externally supplied values including insulin action, insulin sensitivity, insulin-on-board, basal-on-board, anticipated carbohydrate intake, carbohydrate ratio, glycemic index values, blood glucose levels, and/or target blood glucose values.

In further embodiments, the amount of time-shifted basal insulin to be delivered is based on a fixed number of Units of insulin. In other alternative embodiments, the at least one processor determines the amount of time-shifted basal insulin based on blood glucose trends. In some embodiments, the blood glucose trends are supplied to the at least one processor by the user and, in other embodiments, the blood glucose trends are downloaded to the external infusion device from a remote programmer.

In other alternative embodiments, the external infusion device includes at least one alarm to provide alerts to the user. In particular embodiments, the at least one alarm is used to remind the user to deliver time-shifted basal insulin and/or to check blood glucose levels. In yet additional embodiments, the external infusion device further includes a glucose monitoring system to provide current blood glucose data to the at least one processor. In some embodiments, the external infusion device also includes a rate of change alarm to notify the user of changes in blood glucose levels. In further particular embodiments the at least one processor recommends delivery of time-shifted basal insulin upon activation of the rate of change alarm. In alternative embodiments, time-shifted basal insulin is added to a current basal rate and/or a bolus.

According to another embodiment of the invention, an external infusion device delivers insulin from a reservoir into a body of a user. The external infusion device includes at least one drive mechanism operatively couplable to the reservoir to deliver insulin into the body of the user, at least one processor to control the external infusion device, at least one power supply, at least one display device operatively coupled to the at least one processor to provide visual information to the user, at least one input device operatively coupled to the at least one processor to allow the user to command the at least one processor, and a housing. The external infusion device also includes the capability to add time-shifted basal insulin to the user's current basal rate. In some embodiments, the amount of time-shifted basal insulin is selected by the user and, in other embodiments, the amount of time-shifted basal insulin is selected by the at least one processor.

In alternative embodiments, the amount of time-shifted basal insulin is based on externally supplied values including insulin action, insulin sensitivity, insulin-on-board, basal-on-board, anticipated carbohydrate intake, carbohydrate ratio, glycemic index values, blood glucose levels, and/or target blood glucose values. In still other embodiments, the amount of time-shifted basal insulin is based on a percentage of the user's current basal rate. In particular embodiments, the user determines the percentage of current basal rate to add and, in other embodiments, the processor recommends the percentage of current basal rate to add. In further additional embodiments, the percentage of current basal rate is based on externally supplied values including insulin action, insulin sensitivity, insulin-on-board, basal-on-board, anticipated carbohydrate intake, carbohydrate ratio, glycemic index values, blood glucose levels, and/or target blood glucose values.

In other embodiments, the amount of time-shifted basal insulin is based on a fixed number of Units of insulin. In further alternative embodiments, the at least one processor recommends the amount of time-shifted basal insulin based on blood glucose trends supplied to the at least one processor by the user or downloaded from a remote programmer. In still additional embodiments, the external infusion device further includes at least one alarm to provide alerts to the user. In some embodiments, the alarm is used to remind the user to deliver time-shifted basal insulin, and, in other embodiments, the alarm is used to remind the user to check blood glucose levels. In still additional embodiments, the external infusion device further includes a glucose monitoring system to provide current blood glucose data to the at least one processor.

In alternative embodiments, the external infusion device also includes a rate of change alarm to notify the user of changes in blood glucose levels. In particular embodiments, the at least one processor recommends delivery of time-shifted basal insulin upon activation of the rate of change alarm. In additional particular embodiments, time-shifted basal insulin is also added to at least one bolus.

According to yet another embodiment of the invention, an external infusion device delivers insulin from a reservoir into a body of a user. The external infusion device includes at least one drive mechanism operatively couplable to the reservoir to deliver insulin into the body of the user, at least one processor to control the external infusion device, at least one power supply, at least one display device operatively coupled to the at least one processor to provide visual information to the user, at least one input device operatively coupled to the at least one processor to allow the user to command the at least one processor, and a housing. The external infusion device also includes the capability to add time-shifted basal insulin to at least one bolus. In some embodiments, the amount of time-shifted basal insulin added to the at least one bolus is selected by the user. In other embodiments, the amount of time-shifted basal insulin added to the at least one bolus is selected by the at least one processor. In still further embodiments, the amount of time-shifted basal insulin is based on externally supplied values including insulin action, insulin sensitivity, insulin-on-board, basal-on-board, anticipated carbohydrate intake, carbohydrate ratio, glycemic index values, blood glucose levels, and/or target blood glucose values.

In alternative embodiments, the at least one processor includes at least one customizable bolus delivery profile made up of different percentages of multiple bolus delivery profiles including a square wave bolus, a dual wave bolus, a normal bolus, a meal bolus, and/or a time-shifted basal insulin bolus. In still other embodiments, the amount of time-shifted basal insulin is based on a percentage of the user's current basal rate. In particular embodiments, the user determines the percentage of a current basal rate, and, in other embodiments, the at least one processor recommends the percentage of a current basal rate. In further embodiments, the percentage is based on externally supplied values including insulin action, insulin sensitivity, insulin-on-board, basal-on-board, anticipated carbohydrate intake, carbohydrate ratio, glycemic index values, blood glucose levels, and/or target blood glucose values.

In additional embodiments, the amount of time-shifted basal insulin is based on a fixed number of Units of insulin. In alternative embodiments, the at least one processor determines the amount of time-shifted basal insulin based on blood glucose trends supplied to the external infusion device by the user and/or downloaded from a remote programmer. In still other embodiments, the external infusion device further includes at least one alarm to provide alerts to the user. In particular embodiments, the at least one alarm is used to remind the user to deliver time-shifted basal insulin, and, in other embodiments, the at least one alarm is used to remind the user to check blood glucose levels. In alternative embodiments, the external infusion device further includes a glucose monitoring system to provide current blood glucose data to the at least one processor. In particular embodiments, the external infusion device also includes a rate of change alarm to notify the user of changes in blood glucose levels. In additional embodiments, the at least one processor recommends delivery of time-shifted basal insulin upon activation of the rate of change alarm. In yet additional embodiments, the time-shifted basal insulin is also added to the user's current basal rate.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, where like numerals designate corresponding parts or cross-sections in the several figures.

DETAILED DESCRIPTION OF THE PREFERRED EMBODIMENTS

Figure 1:
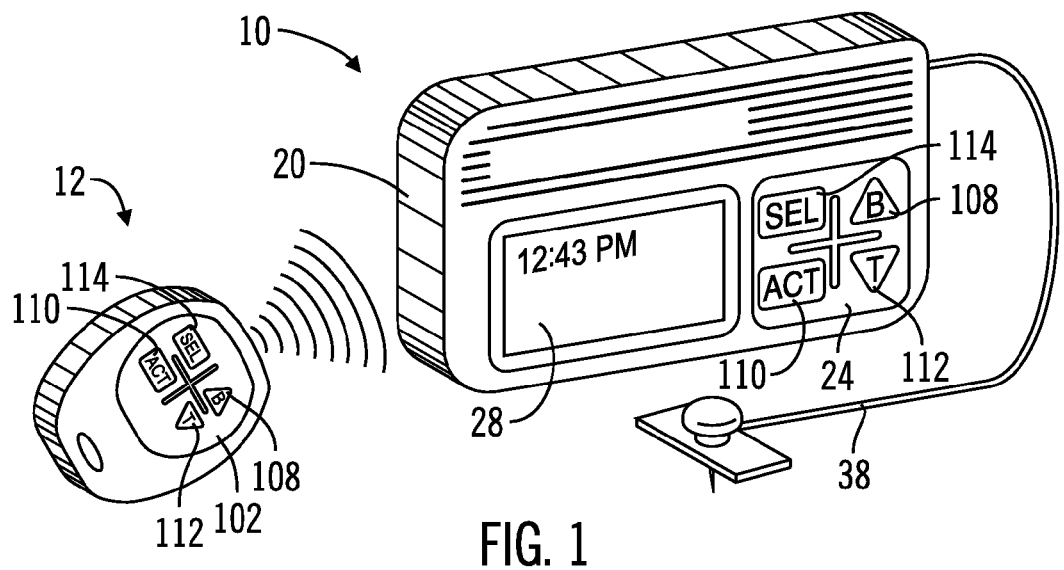
FIG. 1 is a perspective view of an embodiment of an infusion device in accordance with an embodiment of the present invention.

As shown in the drawings for purposes of illustration, the invention is embodied in an infusion device with programmable capabilities to time-shift basal insulin. In particular embodiments of the present invention, a time-shifting basal insulin feature is activated to cover high glycemic index (GI) foods and prevent post-meal hyperglycemia. In further embodiments, time-shifting basal insulin enables fast correction of blood glucose levels in the event an infusion device user misjudges the carbohydrate content of a meal. Additional embodiments provide time-shifting basal insulin features allowing the user to cover high GI foods with basal insulin.

In certain embodiments, the invention is embodied in an infusion device for infusion of a fluid, such as medication, chemicals, enzymes, antigens, hormones, vitamins or the like, into a body of a user. In particular embodiments of the present invention, the infusion device is an external infusion device (or pump), which includes an optional RF programming capability, a bolus capability and/or alarm capability. Embodiments are directed towards use in humans; however, in alternative embodiments, the external infusion devices may be used in animals.

Figure 2:
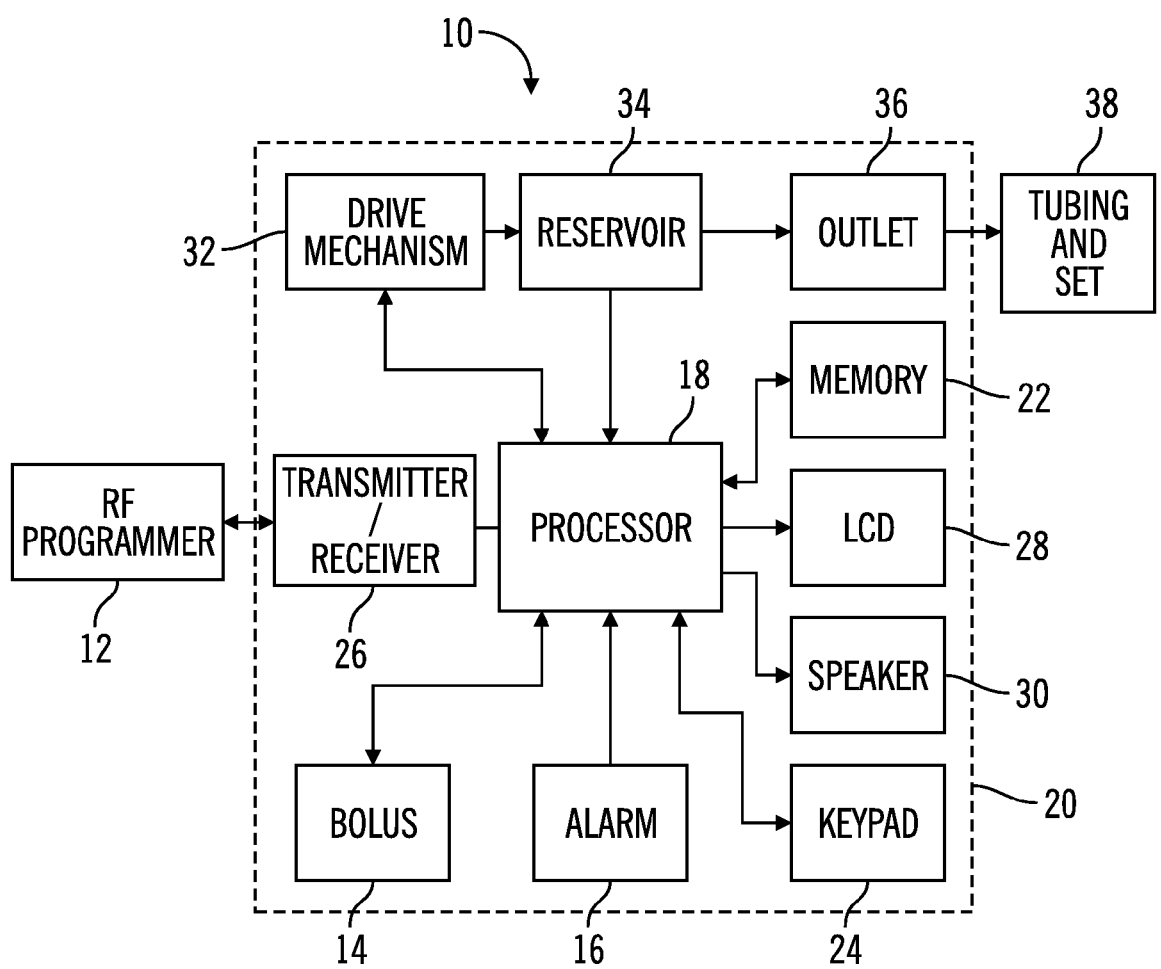
FIG. 2 is a simplified schematic view of the embodiment of FIG. 1.

As illustrated in FIGS. 1 and 2, embodiments of the external infusion device 10 include an optional remote RF programmer 12, a bolus capability 14 and/or an alarm 16. The RF programmer 12 and bolus capability 14 communicate with a processor 18 contained in a housing 20 of the external infusion device 10. The processor 18 is used to run programs and control the external infusion device 10, and is connected to an internal memory device 22 that stores programs, historical data, user defined information and parameters. In particular embodiments, the memory device is a Flash memory and SRAM; however, in alternative embodiments, the memory device 22 may include other memory storage devices such as ROM, DRAM, RAM, EPROM, dynamic storage such as other flash memory, energy efficient hard-drive, or the like. In other embodiments, the external infusion device 10 is an external infusion pump that is programmed through a keypad 24 on the housing 20 or by commands received from the RF programmer 12 through a transmitter/receiver 26. Feedback from the external infusion device 10 on status or programming changes are displayed on an LCD 28 and/or audibly through a speaker 30. In alternative embodiments, the keypad 24 may be omitted and the LCD 28 may be used as a touch screen input device or the keypad 24 may utilize more keys or different key arrangements then those illustrated in the figures. The processor 18 is also coupled to a drive mechanism 32 that is connected to a fluid reservoir 34 containing fluid that is expelled through an outlet 36 in the reservoir 34 and housing 20, and then into a body of a user through tubing and a set 38. In further alternative embodiments, the keypad 24, LCD 20, and speaker 24 may be omitted from the external infusion device, and all programming and data transfer is handled through the RF programmer 12.

Generally, in particular embodiments of the external infusion device 10 are an external insulin pump having the capability to deliver 0 to 35 Units/hour in basal rates and up to 25.0 Units per meal bolus of U-100 Insulin. In alternative embodiments, the external pump delivers other concentrations of insulin, or other fluids, and may use other limits on the delivery rate. In additional embodiments, the external infusion device may support fluid delivery in U-400, U-250, U-200, U-100, U-50, and/or U-40 concentrations of insulin. In still further embodiments the external infusion device may support fluid delivery in insulin concentrations below U-40 and/or above U-500. To deliver a bolus with the keypad the user uses the keypad 24 and keys 108, 110, 112 and/or 114 to program and/or deliver one or more bolus types through a single touch key or by the use of one or more menus. In alternative embodiments, the user can program and/or deliver a bolus with the optional RF programmer 12.

Examples of different bolus types and how to program and/or deliver a bolus can be found in U.S. Pat. No. 6,554,798 issued on Apr. 29, 2003 to Mann et al., and entitled "External Infusion Device with Remote Programming, Bolus Estimator and/or Vibration Alarm Capabilities", which is specifically incorporated by reference herein. In some embodiments, to program and deliver a bolus, the user will press the "B" or Up arrow key 108 in the upper right hand corner of the RF programmer 12 keypad 102. In these examples, units are an increment of insulin. Alternative embodiments, may define units to be any fluid volume, such as micro-liters, ccs, or the like, with the volume being dependent on the type of fluid to be infused. If the user exceeds the desired setting he can wait for an error signal, visual indications, such as flashing, icons, or the like, sound indications such as a "raspberry" type sound, buzzing, tones, sound from a MIDI file, sound from an MP3 file, sound from a WAV file, music or the like, or tactile indications, such as vibration, or the like, and/or any combination of the above, and then press the Up arrow key 108 to begin the process again.

When the desired bolus amount is programmed, the user presses the "activate" or ACT key 110 in the lower left corner of the keypad 24 (or keypad 102 on the RF programmer 12). The external infusion device 10 will then confirm the bolus amount. In alternative embodiments, a visual display or vibration may be used instead of or in addition to audible beeps. To deliver the bolus, the user will then press the ACT key 110 again to start delivery of the bolus. Alternatively, the external infusion device 10 may provide an audible indication by speech.

The bolus delivery will commence after the user confirms the bolus amount selection by pressing the ACT key 110 once again. To cancel this bolus before it starts, the user may either allow the external infusion device 10 to time out and return to the time display or press the Down arrow key 112. Either of these will be accompanied by a "raspberry" type beep, and/or other indications as described above, indicating the bolus has been cleared. Preferably, a standard time-out delay of 15 seconds applies to all key presses involved during the bolus amount selection, but other time periods may be used.

In particular embodiments, a BOLUS element, the word DELIVERY, and the updated amount delivered will be displayed on the LCD 28 while delivery is in progress. The external infusion device 10 will beep once, and/or provide other indications as described above, at the end of the dose.

In particular embodiments, the processor provides recommendations for the amount of insulin to be delivered using a bolus. This recommendation may be based on information including current blood glucose level readings, insulin-on-board, insulin sensitivity, information related to the external infusion device, anticipated carbohydrate intake at meals, Glycemic Index (GI) of food, or the like. Examples of how the processor provides recommendations, or bolus estimation, may be found in U.S. Pat. No. 6,554,798 issued on Apr. 29, 2003 to Mann et al., and entitled "External Infusion Device with Remote Programming, Bolus Estimator and/or Vibration Alarm Capabilities," U.S. patent application Ser. No. 10/996,136 filed Nov. 22, 2004 and entitled "Improved Infusion Device Menu Structure and Method of Using the Same," and U.S. patent application Ser. No. 10/025,052 filed Dec. 19, 2001, and entitled "Medication Delivery System and Monitor," all of which are specifically incorporated by reference herein.

In particular embodiments, the external infusion device allows the user to set a basal rate of insulin delivery (or background insulin) to be delivered continuously (near-continuously, intermittently, pulsed, or the like) throughout the day and night for normal body functions. The basal rate may be adjusted by the user depending on what activities the he or she is engaged in. For example, when the user exercises, the basal rate can be reduced to assure the user's blood glucose does not drop too low. If the user is sick, he or she can increase the basal rate so their blood glucose does not go too high.

In additional embodiments, the user has the capability to give a bolus, or deliver insulin on demand. As described in U.S. Pat. No. 6,554,798, various bolus types (delivery profiles) exist for external infusion devices including a meal bolus, correction bolus, square wave bolus, dual wave bolus, normal bolus, or the like. The processor 18 of the external infusion device may assist the user in determining the amount of the bolus to be delivered. For example, the amount of the meal bolus may be lower or higher based on user's anticipated carbohydrate intake at meals. In particular embodiments, the bolus estimator described in U.S. Pat. No. 6,554,798 assists the user in making such therapy decisions.

Various bolus types may be used to deliver insulin on demand using the external infusion device. For example, an extended bolus (such as a square wave bolus, ramp bolus, triangular bolus, profiled bolus or the like) is a bolus that is delivered over an extended period of time rather than all being delivered at once. An extended bolus may include choices that allow the user and/or processor 18 to choose the type of bolus to be delivered as an extended bolus. A dual wave bolus (FIG. 5(c)) is a combination of a normal (or immediately given) bolus (FIG. 5(a)) with a square wave bolus (FIG. 5(b)). In addition to various bolus types, the user may also program the external infusion device to deliver insulin at a rate throughout the day (basal rate). At some points however, they user may determine that more or less insulin is needed and may command the processor 18 to deliver more or less insulin for a particular period of time, known as a temporary basal rate. In alternative embodiments, the user may also command the processor 18 to suspend insulin delivery altogether for a particular amount of time.

The bolus estimator, as described in U.S. Pat. No. 6,554, 798, may be used to assist the external infusion device 10 user with the estimations that are done to determine the proper bolus amount that is needed to cover the anticipated carbohydrate intake at meals. The bolus estimator 14 does this by suggesting a bolus based on a carbohydrate ratio (pre-programmed or manually set) that is stored in the memory 22 of the external infusion device 10. The bolus estimator 14 will also take into account the user's insulin sensitivity and the differential between the user's pre-programmed target blood glucose (BG) level and the user's current BG level at the time the carbohydrate estimator 14 is activated. The recommendation, or result of the bolus estimator 14, is sometimes referred to as a "correction bolus". The bolus estimator uses user defined values to determine appropriate estimations and/or recommendations including target blood glucose, insulin sensitivity, and carbohydrate ratio.

A user's target blood glucose value is the blood glucose value the user would like to achieve. Generally, the programmable blood glucose (BG) values for this range are between 60 to 200 in five unit increments. Preferably, the carbohydrate calculator has the capability to accept values that range between 20 to 600 in 1 unit increments to cover a large number of possible scenarios. However, in alternative embodiments, different ranges and increments may be used.

Insulin sensitivity is a value that reflects how far the user's blood glucose drops in milligrams per deciliter (mg/dl) when one unit of insulin is taken. In some embodiments, the programmable values for this range are between 5 to 180 in one unit increments. However, in alternative embodiments, different ranges and increments may be used.

Carbohydrate ratio is a value that reflects the amount of carbohydrates that are covered by one unit of insulin. Generally, the values are in the range of 1 to 300 in increments of 1 unit (or, alternatively, in ranges of 0.1 to 5.0 in increments of 0.1 for carbohydrate exchanges). In some embodiments, the programmable values for this range are between 5 to 30 in one unit increments. However, in alternative embodiments, different ranges and increments may be used.

In particular embodiments, the external infusion device may also take into account the Glycemic Index (GI) of food. The GI value is a ranking of carbohydrates based on their immediate effect on blood glucose levels. Carbohydrates that break down quickly during digestion have high GI values. The blood glucose response to high GI foods is fast and high. GI values are ranked on a scale of 1 to 100 according to the extent to which they raise blood glucose levels after consumption. The marked fluctuations of blood glucose levels immediately after consumption of high GI foods may be a cause for concern for many diabetics, particularly those relying on external infusion devices for insulin delivery. In some embodiments of the invention, the user may take into account the GI values of food to effectively manage their blood glucose levels. Foods having high GI values that cause fast and high blood glucose responses include, for example, boiled white rice (139), Cornflakes™ (92), Gatorade® (89), Power Bars® (83), English Muffins (77), and the like. Foods having low GI values that cause a slower rise in blood glucose levels include, for example, pizza (30), peanuts (13), soup (1) and the like.

In alternative embodiments, the bolus estimator may take into account the effects of recently taken insulin that is still, at least partially, still active in the body of the user. The concern would be that the remaining insulin could have the effect of lowering the blood glucose level too quickly, or too far, if the remaining insulin was not accounted for. This value is known as the "insulin duration factor" and it accounts for effects of insulin still remaining in the body. In particular embodiments, the insulin duration factor may be selected by the healthcare professional or the user upon recommendation and/or consultation with the healthcare professional.

In physiological terms, an early insulin response to a sudden increase in glucose level results in less total insulin being needed to bring the glucose level back to a desired glucose level. This is because the infusion of insulin increases the percentage of glucose that is taken up in the body. Infusing a large amount of insulin to increase the percentage of glucose uptake while glucose concentration is high results in an efficient use of insulin. Conversely, infusing a large amount of insulin while the glucose concentration is low results in using a large amount of insulin to remove a relatively small amount of glucose. The infusion of less total insulin helps to avoid development of insulin resistance in the user. As well, first-phase insulin is thought to result in an early suppression of hepatic glucose output.

Figure 3:
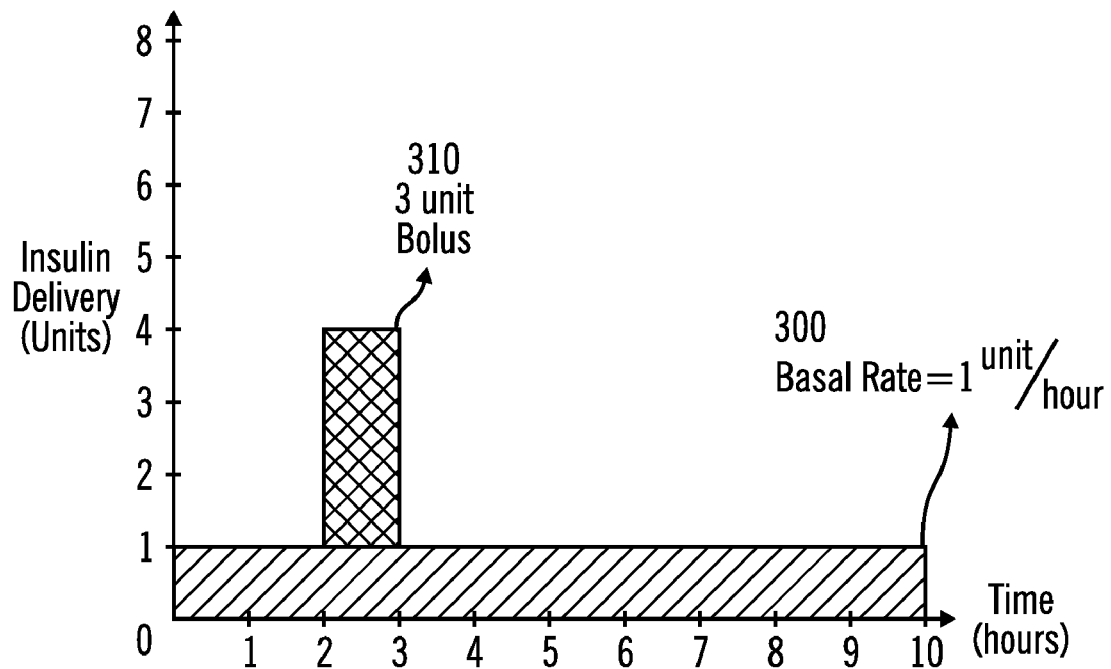
FIG. 3 is a plot of insulin delivery over time in accordance with an embodiment of the present invention.
Figure 4:
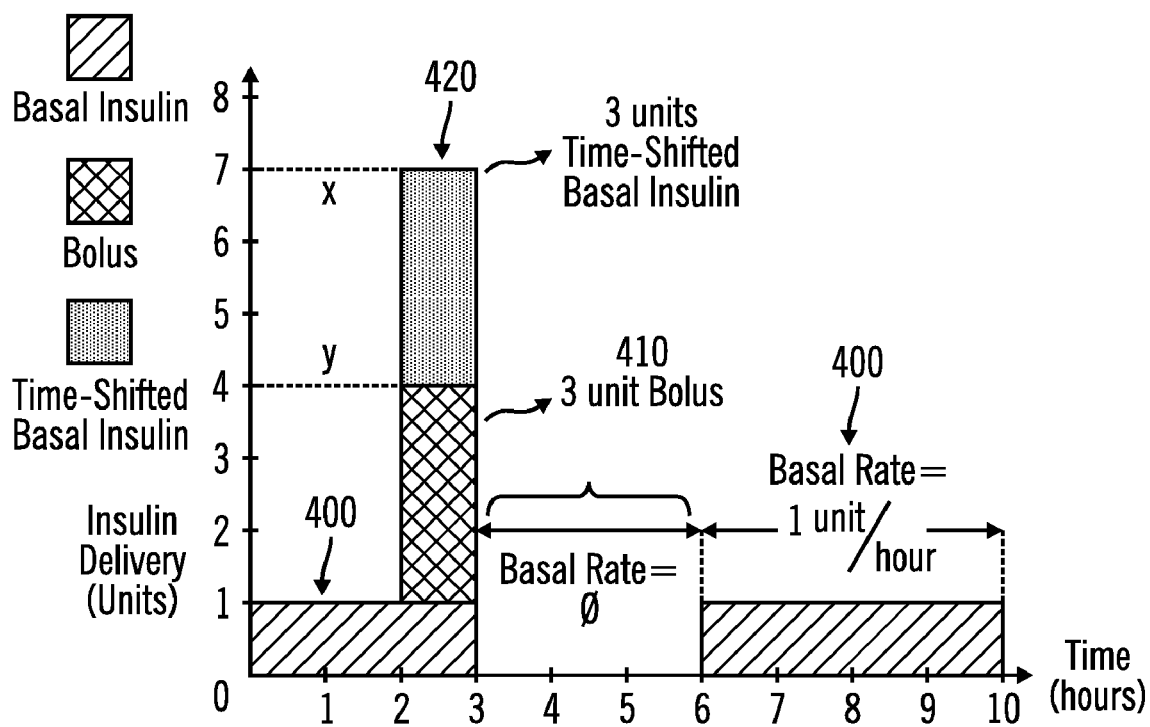
FIG. 4 is a plot of insulin delivery over time using time-shifted basal insulin in accordance with an embodiment of the present invention.

In particular embodiments, the external infusion device may include the capability to deliver time-shifted basal insulin. Time-shifting basal insulin is the process by which a portion of basal insulin (i.e., a two, three, or four hour block of basal insulin) is added to a bolus or current basal rate. To more clearly describe the time-shifting process, a standard plot of insulin delivery from an external infusion device is shown in FIG. 3. In FIG. 3, between the hours of 12:00 pm and 10:00 pm, the external infusion device continuously delivers insulin at a rate 300 of 1 Unit/hour (basal rate). At 2:00 pm, a three unit bolus 310 is delivered to the user to prepare for an upcoming meal (meal bolus). In contrast, FIG. 4 shows a similar graph of insulin delivery from an external infusion device using time-shifted basal insulin. In this figure, the basal rate 400 from 12:00 pm to 3:00 pm is 1 Unit/hour. Again, a three unit bolus 410 is delivered at 2:00 pm. However, as shown in FIG. 4, a block of basal insulin 420 that was to be delivered between the hours of 3:00 pm to 6:00 pm has been time-shifted and added to the bolus 410 for immediate delivery at 2:00 pm. Accordingly, in this example, basal insulin delivery is suspended between the hours of 3:00 pm and 6:00 pm to account for the insulin added to the bolus.

In alternative embodiments, shifting may occur in 5 minute, 10 minute, 15 minute, 30 minute, or 60 minute intervals. In other embodiments, the increments may be customizable to any increment desired by the user. In still additional embodiments, the increments and lengths may be fixed at the time of manufacture or original programming. In further embodiments, the blocks of time may be as short as 5 minutes and as long as 12 hours.

In particular embodiments, utilizing time-shifted basal insulin may allow the user to deliver more bolus insulin more quickly to speed correction of hyperglycemia and/or account for consumption of high GI foods. When a user chooses to consume foods with high GI values, he or she must be prepared for fast and high fluctuations in blood glucose levels. High GI foods have the effect of raising blood glucose levels immediately after consumption. As described above, infusing a large amount of insulin to increase the percentage of glucose uptake while glucose concentration is high results in an efficient use of insulin. Effectively controlling blood glucose levels after consumption of high GI foods may be carried out by adding time-shifted basal insulin to the meal bolus delivered to cover the anticipated carbohydrate intake. Conversely, a suspension (and/or reduction) in basal insulin, corresponding to the amount of time-shifted basal insulin added to the bolus, prevents hypoglycemia one to two hours after the high GI food is ingested. By adding the basal insulin to the presently delivered bolus, more insulin becomes immediately available to the user. The corresponding suspension (and/or reduction) in basal insulin prevents hypoglycemia in the hours subsequent to delivery of the bolus. In particular embodiments, consumption of high GI foods necessitates delivery of time-shifted insulin because high GI foods cause fast and high blood glucose responses. In these embodiments, fast and high blood glucose responses require more insulin to be delivered on the front end (immediately prior to consumption) and less insulin needed on the back end (one to two hours after consumption); a process that is carried out by utilizing time-shifted basal insulin.

The physiological affects insulin has on glucose concentration in the user's interstitial fluid further clarifies the advantages of using time-shifted basal insulin. The external infusion device delivers insulin via tubing, set and a cannula 38 (FIG. 2) to the user's interstitial fluid. The insulin diffuses from the local interstitial fluid surrounding the cannula into the blood plasma and then spreads throughout the body in the main circulatory system. The insulin then diffuses from the blood plasma into the interstitial fluid substantially throughout the entire body. The insulin then binds with and activates membrane receptor proteins on cells of body tissues. This facilitates glucose permeation into the activated cells. The tissues of the body take up glucose from the interstitial fluid. As the glucose level in the interstitial fluid decreases, glucose diffuses from the blood plasma into the interstitial fluid to maintain glucose concentration equilibrium. A more detailed explanation of the physiological effects of insulin can be found in U.S. Pat. No. 6,558,351 issued on May 6, 2003 to Steil et al., and entitled "Closed Loop System For Controlling Insulin Infusion," which is specifically incorporated by reference herein.

In other embodiments, if a user misjudges their anticipated carbohydrate intake, they may end up giving a lower bolus than is actually required. This may cause their resulting post-meal blood glucose level to be too high. Upon learning of the high BG levels, the user may respond by delivering a correction bolus. If the user chooses to deliver a simple correction bolus, while maintaining basal delivery, their blood glucose levels may indeed drop to a target range immediately after delivery, however, continued basal delivery coupled with the correction bolus may cause their BG levels to drop too low one to two hours after delivery of the correction bolus and ultimately cause hypoglycemia. In contrast, delivering a bolus with time-shifted basal insulin has many advantages. When the user and/or processor choose to add time-shifted basal insulin to the bolus, their basal insulin for the next two to four hours is turned into an immediate bolus delivery. This method has the advantage of bringing the user back to a target range more quickly by delivering more insulin sooner. Additionally, this method accounts for the early delivery of basal insulin by suspending (and/or reducing) a corresponding amount of basal insulin to be delivered, which ultimately prevents hypoglycemia in the hours following delivery of the correction bolus.

In further embodiments, when added to a bolus, time-shifted basal insulin increases the speed at which the bolus works. In particular embodiments, time-shifted basal insulin helps cover high GI foods by aiding in prevention of hyperglycemia immediately after consumption, and correspondingly aiding in the prevention of hypoglycemia in the hours following bolus delivery. In some embodiments, a one hour block of basal insulin is delivered as a bolus to speed its effect. In other embodiments, two, three and/or four blocks of basal insulin may be delivered as a bolus to speed its effect. In still further embodiments, the amount of basal insulin that is to be delivered may be preprogrammed on the external infusion device. In other embodiments, the amount of basal insulin that is to be delivered may be programmable by the user and/or healthcare professional. In alternative embodiments, the amount of basal insulin that can be added to a bolus may have a maximum threshold value that the user cannot override.

In some embodiments, complex algorithms may be utilized to make certain that the user does not go hypoglycemic when suspending (and/or reducing) basal insulin as described above. Although a bolus delivered with time-shifted basal insulin may be effective for controlling blood glucose levels after consumption of high GI foods, a possibility may exist that the suspension (and/or reduction) in basal delivery one to two hours after the bolus may cause hypoglycemia if all of the suspended insulin is applied to the bolus. This is due to a more efficient use of insulin with high glucose levels, leaving excess insulin in the blood stream that could drive glucose levels too low. To compensate for this, the user may suspend basal delivery and transfer only a portion of the basal insulin. Thus, getting benefits of returning to the normal range more quickly without avoiding lows. These situations may occur depending on a number of factors including the user's insulin sensitivity, body type, body weight, physical activity, normal carbohydrate intake, and the like.

The portion of insulin shifted may be determined by a proportional rule, or other algorithmic approach that analyzes anticipated reactions. The adjustments may be based on Glycemic Index (GI), current glucose levels, glucose level trends, past experience, user specific variables (as discussed above), alone or in combination, or the like. In particular embodiments, the portion amount corrected is user selectable. In alternative embodiments, the portion may be determined automatically or semi-automatically with the aid of a wizard.

In alternative embodiments, the processor 18 of the external infusion device may also query the user to determine the time-shifting duration (i.e., should a one, two, three, or four hour block of basal insulin be converted). This consideration is important in assuring that the user does not suspend basal delivery for a prolonged period of time. Accordingly, in some embodiments, the time-shifting duration may include a maximum and/or minimum threshold amount that cannot be adjusted by the user. In other embodiments, the user may adjust the maximum and/or minimum time-shifting duration values based on their individualized treatment. In yet additional embodiments, the processor 18 of the external infusion device may determine time-shifting duration based on insulin action, insulin sensitivity, insulin-on-board, basal on board, carbohydrate ratio, anticipated carbohydrate intake, blood glucose levels, target blood glucose values and the like.

In still additional embodiments, time-shifted basal insulin may be a percentage of the user's current basal rate. In these embodiments, the processor 18 of the external infusion device may query the user to enter in a total percentage of the basal rate to deliver as an immediate bolus and/or add to a prescheduled bolus delivery. In further embodiments, the processor 18 may recommend a percentage of the basal rate to convert based on externally supplied values including insulin action, insulin sensitivity, insulin-on-board, basal on board, carbohydrate ratio, anticipated carbohydrate intake, blood glucose levels, target blood glucose values and the like.

In further particular embodiments, the external infusion device may add a fixed number of Units of time-shifted basal insulin to each bolus delivered. In some embodiments, the fixed number of Units of time-shifted basal insulin may be added to a meal bolus only. In additional embodiments, the processor 18 of the external infusion device may automatically add time-shifted basal insulin to each bolus programmed by the user in accordance with the user's individualized treatment. In some embodiments, the user may be able to adjust the amount of time-shifted basal insulin added to each bolus, and in other embodiments, the amount added may be predefined by a healthcare professional.

In still further embodiments, the external infusion device processor 18 may use blood glucose trends to affect the amount of time-shifted basal insulin added to a bolus. In these embodiments, the processor 18 may utilize the user's blood glucose (BG) data to calculate BG trends. In some embodiments, the BG data may be directly obtained from a glucose monitor, a glucose meter and/or a continuous glucose monitoring system such as Medtronic MiniMed's Guardian® RT CGMS or the Therasense Navigator®. In other embodiments, the BG data along with the BG trends may be downloaded directly from a remote programmer, computer and/or program (i.e., Medtronic CareLink® described below). In still further embodiments, trends may also be based on insulin action, insulin sensitivity, insulin-on-board, basal on board, carbohydrate ratio, anticipated carbohydrate intake, blood glucose levels, target blood glucose values and the like. These values may be entered directly into the external infusion device by the user, downloaded from a computer, or entered into the external infusion device using a remote programmer via wired and/or wireless communication.

In alternative embodiments, the amount of time-shifted basal insulin added to a bolus may be based on the insulin-on-board (IOB) value, which is based upon an estimate of the amount of active insulin currently remaining in the body. In still other embodiments, the external infusion device may include a food library containing nutritional information. The nutritional information may include fat content, protein content, sugar content, and the like. In some embodiments, the user may determine the amount of time-shifted basal insulin to add to a meal bolus based on nutritional information provided by the external infusion device along with their anticipated carbohydrate intake.

Figure 5:
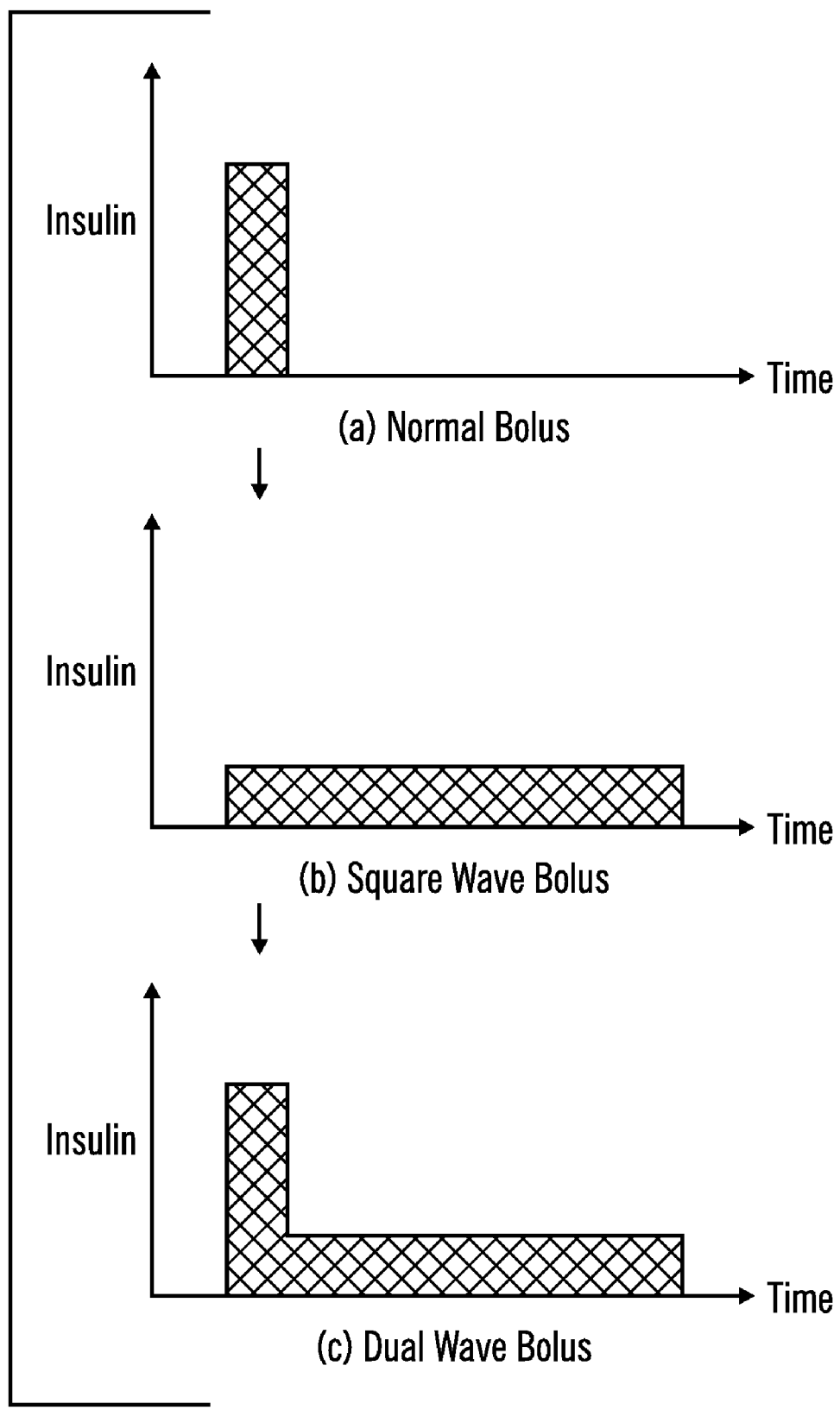
FIG. 5 is a plot of a normal bolus, square wave bolus and dual wave bolus in accordance with an embodiment of the present invention.

In additional alternative embodiments, the user may command the processor 18 of the external infusion device to alter the shape of a square wave bolus delivery profile. A standard square wave bolus delivery profile is shown in FIG. 5(*b*). By altering the shape of the square wave bolus delivery profile, the user can effectively deliver an early bolus.

In other embodiments, the user may have the capability to deliver time-shifted basal insulin in response to a rate of change alarm included in the external infusion device. When the external infusion device is coupled to continuous glucose monitoring system, a rate of change alarm may be included to warn the user of changes in BG levels. In these embodiments, the user and/or processor may choose to deliver time-shifted basal insulin in addition to or in place of a correction bolus to bring BG levels back to target ranges more quickly.

Figure 6:
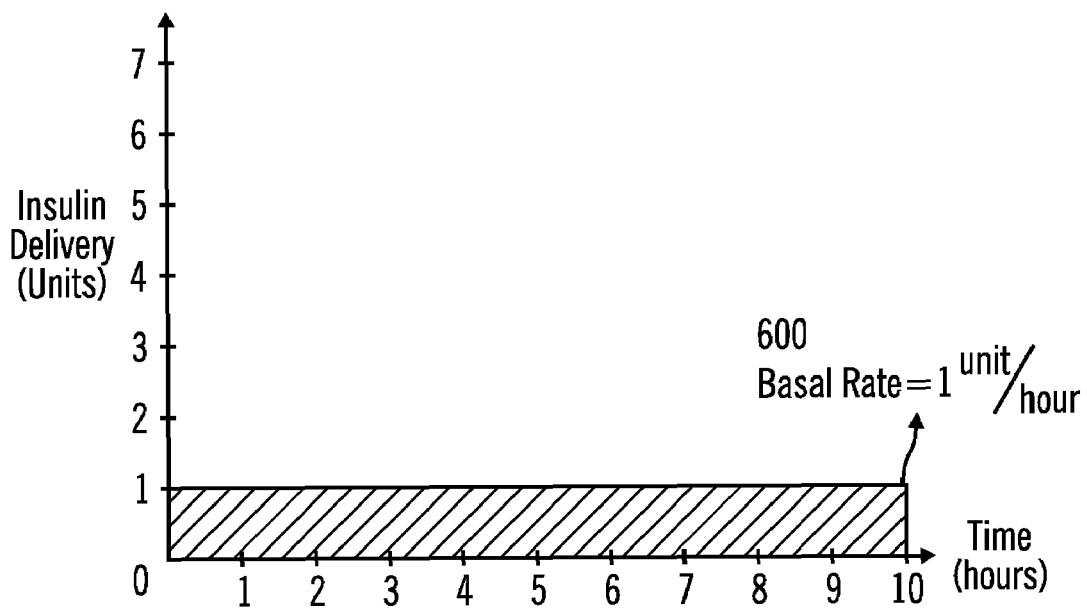
FIG. 6 is yet another plot of insulin delivery over time in accordance with another embodiment of the present invention.
Figure 7:
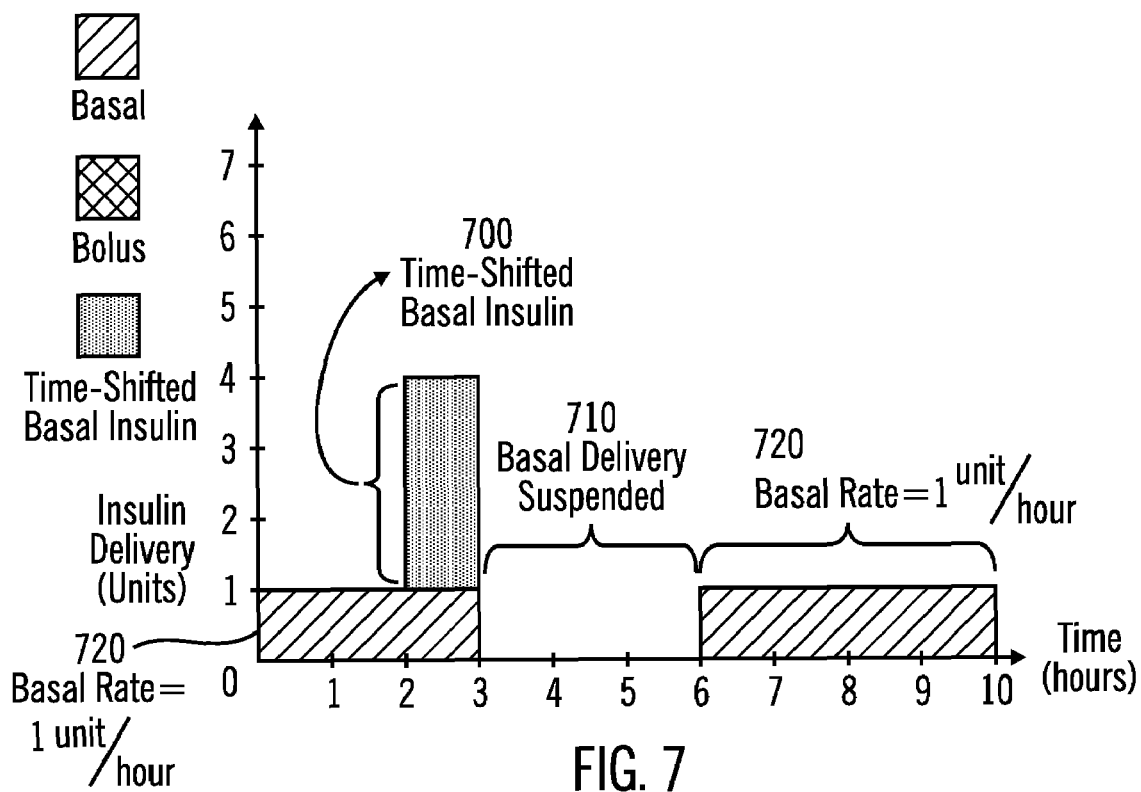
FIG. 7 is another plot of insulin delivery over time using time-shifted basal insulin in accordance with an alternative embodiment of the present invention.

In alternative embodiments, time-shifted based insulin may be added to the user's current basal rate instead of being added to a bolus. FIG. 6 shows a graph of insulin delivery (Units) vs. time (hours). The basal rate 600 in FIG. 6 is 1 Unit/hour. When the user and/or processor 18 activate the time-shifted basal insulin feature, the user and/or processor 18 first choose the amount of basal insulin to add to the current basal rate as shown in FIG. 7. In FIG. 7, the block of basal insulin 700 to be delivered between the hours of 3:00 pm and 6:00 pm is added to the user's current basal rate at 2:00 pm. Basal delivery is therefore suspended during the block of time 710 between 3:00 pm and 6:00 pm. In the present embodiment, the time-shifted basal insulin added to the user's current basal rate 720 may be programmable by the user. In alternative embodiments, the processor 18 may activate the time-shifted basal insulin feature automatically based on externally supplied values including insulin action, insulin sensitivity, insulin-on-board, basal on board, carbohydrate ratio, anticipated carbohydrate intake, blood glucose levels, target blood glucose values and the like. In still further alternative embodiments, the external infusion device may include maximum and/or minimum threshold duration amounts that prevent prolonged suspension of basal insulin delivery. In some embodiments, these thresholds may be user adjustable and in other embodiments, the thresholds may be predefined.

Figure 8:
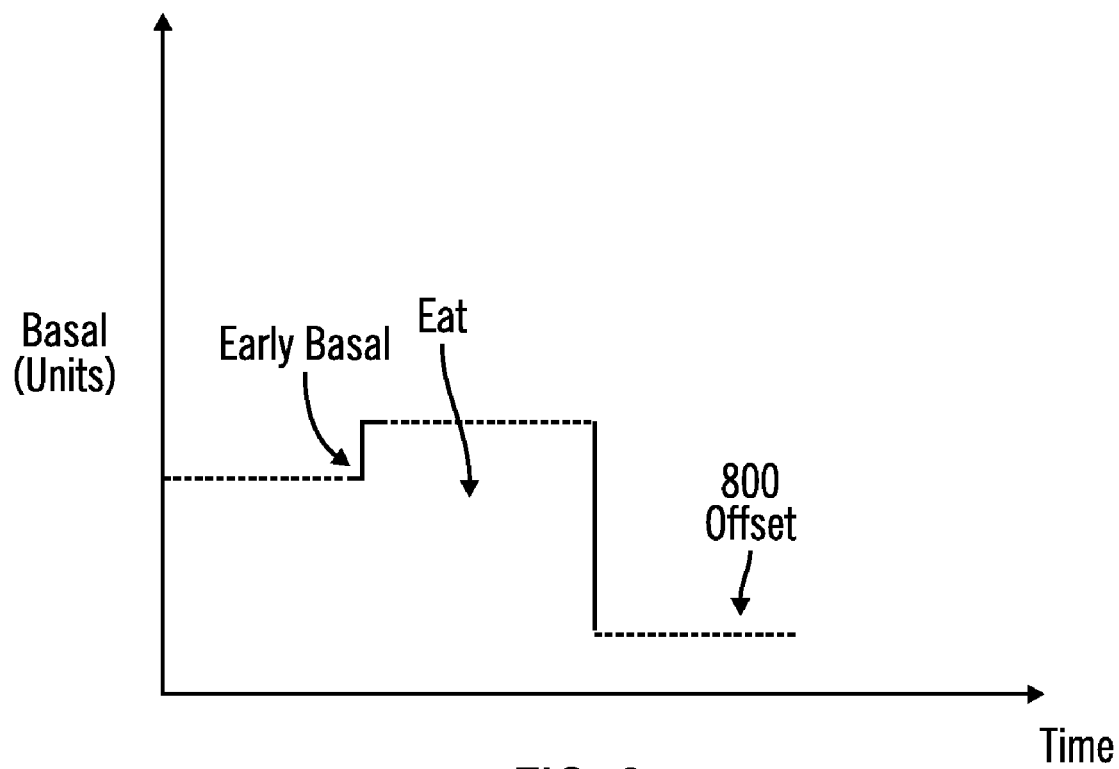
FIG. 8 is a plot of a time-shifted basal insulin offset in accordance with another embodiment of the present invention.

In some embodiments, when time-shifted basal insulin is added to the user's current basal rate, the external infusion device effectively provides early basal delivery or is "pre-meal loading" the user with insulin (FIG. 8). The resulting offset 800 prevents hypoglycemia by assuring the user does not receive too much insulin. In these embodiments, the user may determine that adding time-shifted basal insulin to the current basal rate prior to eating (i.e. 30 minutes before a meal) may prevent the user from giving too much insulin. In alternative embodiments, the user and/or processor 18 may determine the amount of time-shifted basal insulin to add to the current basal rate based on the rate of change of the user's blood glucose.

In further embodiments, the processor 18 may allow the user to add time-shifted basal insulin to a bolus and the current basal rate. In these embodiments, the user may choose to add time-shifted basal insulin to a bolus only, to their current basal rate only, or to a bolus and current basal rate. In other embodiments, the processor 18 may allow the user to add time-shifted basal insulin to multiple bolus types, multiple basal rates, or the like.

Figure 9:
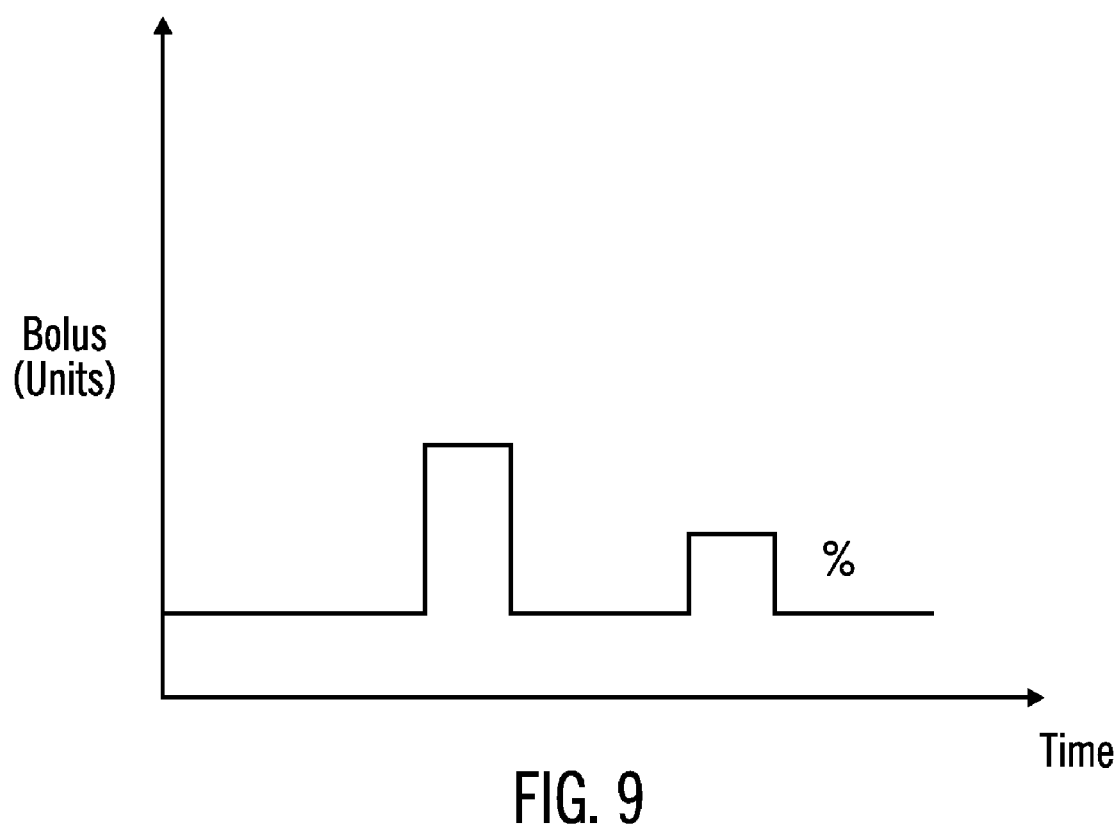
FIG. 9 is a plot of a dual normal bolus in accordance with an embodiment of the present inventions.

In additional embodiments, the external infusion device may include a customizable bolus option. The customizable bolus option may allow the user to select a bolus that includes percentages of predefined bolus types including a normal bolus, dual wave bolus, square wave bolus, correction bolus, meal bolus, time-shifted basal insulin bolus, dual normal bolus (FIG. 9) or the like. For example, the user may select the customizable bolus option to contain a 30% square wave bolus, 30% dual wave bolus, 20% normal bolus, and 20% time-shifted basal insulin bolus. In some embodiments, the selectable range of each profile may be from 0 to 100%. In other embodiments, smaller ranges may be used. In still further embodiments, the external infusion device may include maximum and/or minimum thresholds that are not adjustable by the user. For example, in some embodiments, the selectable range of the time-shifted basal insulin bolus may be from 20% to 50%.

In alternative embodiments, the external infusion may include predefined combinations of customizable bolus options. The predefined combinations may be selectable by the user and delivered on demand to replace normal insulin delivery. However, in alternative embodiments, the processor 18 of the external infusion device may automatically select the most appropriate customizable bolus delivery option based on externally supplied values. These values include insulin action, insulin sensitivity, insulin-on-board, basal on board, carbohydrate ratio, anticipated carbohydrate intake, blood glucose levels, target blood glucose values and the like.

In still further embodiments, the external infusion device may provide graphs showing the user how each customizable bolus delivery profile might affect their overall blood glucose levels for a period of time following delivery. In these embodiments, the user may determine the appropriate customizable bolus to deliver based on reviewing the graphs created by the processor 18 of the external infusion device. In additional embodiments, the graphs and/or data may be downloaded from a computer containing the user's blood glucose data. In some embodiments, the user's downloaded data may include blood glucose data, insulin sensitivity data, and the like.

In still additional embodiments, the external infusion device may be connected to a computer and download insulin delivery recommendations and/or nutritional information of food. For example, in some embodiments, the external infusion device may connect with programs such as Medtronic CareLink® (described in U.S. patent application Ser. No. 10/913,149 filed on Aug. 6, 2004 entitled "Medical Data Management System and Process", which is specifically incorporated by reference herein) to download nutritional content of food and user blood glucose data. In other embodiments, the user's blood glucose trends may be downloaded to assist the processor 18 in providing therapy recommendations to the user. In still additional embodiments, the downloaded data may assist the user and/or processor 18 in determining time-shifted basal insulin amounts to add to a scheduled bolus delivery and/or amounts to be added to the current basal rate.

In alternative embodiments, a time-shifted basal insulin bolus profile may be calculated using a computer and program such as Medtronic CareLink®. The calculated profiles may be determined based on externally supplied values including insulin action, insulin sensitivity, insulin-on-board, basal on board, carbohydrate ratio, anticipated carbohydrate intake, blood glucose levels, target blood glucose values, blood glucose trends and the like. The data may be gathered by a healthcare professional and/or uploaded to the remote by the user. The calculated time-shifted basal insulin bolus may be subsequently downloaded to the external infusion device for delivery to the user.

In still additional embodiments, the external infusion device may include an alarm to remind the user to deliver a bolus, resume and/or change basal delivery, check blood glucose levels, and the like. In some embodiments, the alarm may be used to remind the user to deliver time-shifted basal insulin, a meal bolus, square wave bolus, dual wave bolus, correction bolus, or the like. In other embodiments, the alarm may remind the user to change, suspend or resume basal delivery. In still additional embodiments, the alarm may include an alarm deactivation feature that allows the user to deactivate a scheduled alarm when the user actually delivers the bolus and/or updates the basal delivery. The alarm deactivation feature is more fully explained in U.S. patent application Ser. No. 11/171,010 filed Jun. 29, 2005 and entitled "Infusion Device with Bolus Alarm Deactivation and Method of Using the Same," which is specifically incorporated by reference herein.

In some embodiments, the alarm may provide audible, visual, and/or tactile indications based on user preference. Audible indications may allow use of MP3 type music files that may be downloaded to the external infusion device via standard wired and/or wireless connections to a PC (USB, serial, parallel, firewire, infrared, Bluetooth, RF, and the like). In additional embodiments, the audible indications may include standardized beeps and tones. In further embodiments, the visual indications may include flashing LEDs on the LCD and the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An external infusion device for delivering insulin from a reservoir into a body of a user, the external infusion device comprising:
    at least one drive mechanism operatively couplable to the reservoir to deliver insulin into the body of the user;
    at least one processor to control the external infusion device;
    at least one power supply;
    at least one display device operatively coupled to the at least one processor to provide visual information to the user;

at least one input device operatively coupled to the at least one processor to allow the user to command the at least one processor; and a housing;

wherein the external infusion device is programmed to deliver three different types of basal insulin, the three types of basal insulin including current basal insulin, future basal insulin and time-shifted basal insulin, time-shifted basal insulin being a portion of the future basal insulin that is added to the current basal insulin, the portion of future basal insulin being insulin that is to be delivered during a future time period, the delivery of the time-shifted basal insulin automatically eliminates delivery of the future basal insulin during the future time period.

2. An external infusion device according to claim 1, wherein the amount of time-shifted basal insulin to be delivered is selected by the user.

3. An external infusion device according to claim 1, wherein the amount of time-shifted basal insulin to be delivered is selected by the at least one processor.

4. An external infusion device according to claim 1, wherein the time-shifted basal insulin is added to a current basal rate.

5. An external infusion device according to claim 1, wherein the amount of time-shifted basal insulin to be delivered is based on a fixed number of Units of insulin.

6. An external infusion device according to claim 1, wherein time-shifted basal insulin is added to at least one of a current basal rate and a bolus.

7. An external infusion device according to claim 1, wherein the amount of time-shifted basal insulin to be delivered is based on externally supplied values.

8. An external infusion device according to claim 7, wherein the externally supplied values include at least one of insulin action, insulin sensitivity, insulin-on-board, basal-on-board, anticipated carbohydrate intake, carbohydrate ratio, glycemic index values, blood glucose levels, and target blood glucose values.

9. An external infusion device according to claim 1, wherein the amount of time-shifted basal insulin to be delivered is based on a percentage of a user's current basal rate.

10. An external infusion device according to claim 9, wherein the user determines the percentage of the user's current basal rate to be used.

11. An external infusion device according to claim 9, wherein the at least one processor recommends the percentage of the user's current basal rate to be used.

12. An external infusion device according to claim 9, wherein the percentage of current basal rate is based on externally supplied values including at least one of insulin action, insulin sensitivity, insulin-on-board, basal-on-board, anticipated carbohydrate intake, carbohydrate ratio, glycemic index values, blood glucose level, and target blood glucose value.

13. An external infusion device according to claim 1, wherein the at least one processor determines the amount of time-shifted basal insulin based on blood glucose trends.

14. An external infusion device according to claim 13, wherein the blood glucose trends are supplied to the at least one processor by the user.

15. An external infusion device according to claim 13, wherein the blood glucose trends are downloaded to the external infusion device from a remote programmer.

16. An external infusion device according to claim 1, further including a glucose monitoring system to provide current blood glucose data to the at least one processor.

17. An external infusion device according to claim 16, wherein the external infusion device include a rate of change alarm to notify the user of changes in blood glucose levels.

18. An external infusion device according to claim 17, wherein the at least one processor recommends delivery of time-shifted basal insulin upon activation of the rate of change alarm.

19. An external infusion device according to claim 1, wherein the time-shifted basal insulin is added to at least one bolus.

20. An external infusion device according to claim 19, wherein the at least one processor includes at least one customizable bolus delivery profile.

21. An external infusion device according to claim 20, wherein the at least one customizable bolus delivery profile includes at least one of a square wave bolus, a dual wave bolus, a normal bolus, a meal bolus, and a time-shifted basal insulin bolus.

22. An external infusion device for delivering insulin from a reservoir into a body of a user, the external infusion device comprising:

at least one drive mechanism operatively couplable to the reservoir to deliver insulin into the body of the user;

at least one processor to control the external infusion device;

at least one power supply;

at least one display device operatively coupled to the at least one processor to provide visual information to the user;

at least one input device operatively coupled to the at least one processor to allow the user to command the at least one processor; and a housing;

wherein the external infusion device is programmed to deliver three different types of basal insulin, the three types of basal insulin including current basal insulin, future basal insulin and time-shifted basal insulin, time-shifted basal insulin being a portion of the future basal insulin that is added to the current basal insulin, the portion of the future basal insulin being insulin that is to be delivered during a future time period, the delivery of the time-shifted basal insulin automatically eliminates delivery of the future basal insulin during the future time period; further including at least one alarm to provide alerts to the user.

23. An external infusion device according to claim 22, wherein the amount of time-shifted basal insulin is selected by the user.

24. An external infusion device according to claim 22, wherein the amount of time-shifted basal insulin is selected by the at least one processor.

25. An external infusion device according to claim 22, wherein the amount of time-shifted basal insulin is based on a fixed number of Units of insulin.

26. An external infusion device according to claim 22, wherein time-shifted basal insulin is also added to at least one bolus.

27. An external infusion device according to claim 22, wherein the at least one alarm is used to remind the user to deliver time-shifted basal insulin.

28. An external infusion device according to claim 22, wherein the at least one alarm is used to remind the user to check blood glucose levels.

29. An external infusion device according to claim 22, wherein the amount of time-shifted basal insulin is based on externally supplied values.

30. An external infusion device according to claim 29, wherein the externally supplied values include at least one of insulin action, insulin sensitivity, insulin-on-board, basal-on-board, anticipated carbohydrate intake, carbohydrate ratio, glycemic index values, blood glucose level, and target blood glucose value.

31. An external infusion device according to claim 22, wherein the amount of time-shifted basal insulin is based on a percentage of a user's current basal rate.

32. An external infusion device according to claim 31, wherein the user determines the percentage of the user's current basal rate.

33. An external infusion device according to claim 31, wherein the at least one processor recommends the percentage of the user's current basal rate.

34. An external infusion device according to claim 31, wherein the percentage of current basal rate is based on externally supplied values including at least one of insulin action, insulin sensitivity, insulin-on-board, basal-on-board, anticipated carbohydrate intake, carbohydrate ratio, glycemic index values, blood glucose level, and target blood glucose value.

35. An external infusion device according to claim 22, wherein the at least one processor determines the amount of time-shifted basal insulin based on blood glucose trends.

36. An external infusion device according to claim 35, wherein the blood glucose trends are supplied to the at least one processor by the user.

37. An external infusion device according to claim 35, wherein the blood glucose trends are downloaded to the external infusion device from a remote programmer.

38. An external infusion device according to claim 22, further including a glucose monitoring system to provide current blood glucose data to the at least one processor.

39. An external infusion device according to claim 38, wherein the external infusion device include a rate of change alarm to notify the user of changes in blood glucose levels.

40. An external infusion device according to claim 39, wherein the at least one processor recommends delivery of time-shifted basal insulin upon activation of the rate of change alarm.

41. An external infusion device for delivering insulin from a reservoir into a body of a user, the external infusion device comprising:
at least one drive mechanism operatively couplable to the reservoir to deliver insulin into the body of the user;
at least one processor to control the external infusion device;
at least one power supply;
at least one display device operatively coupled to the at least one processor to provide visual information to the user;
at least one input device operatively coupled to the at least one processor to allow the user to command the at least one processor; and
a housing;
wherein the external infusion device is programmed to deliver three different types of basal insulin, the three types of basal insulin including current basal insulin, future basal insulin and time-shifted basal insulin, time-shifted basal insulin being a portion of the future basal insulin that is added to the current basal insulin and to at least one bolus, the portion of future basal insulin being insulin that is to be delivered during a future time period, the delivery of the time-shifted basal insulin automatically eliminates delivery of the future basal insulin during the future time period.

42. An external infusion device according to claim 41, wherein the amount of time-shifted basal insulin is selected by the user.

43. An external infusion device according to claim 41, wherein the amount of time-shifted basal insulin is selected by the at least one processor.

44. An external infusion device according to claim 41, wherein time-shifted basal insulin is also added to the user's current basal rate.

45. An external infusion device according to claim 41, wherein the amount of time-shifted basal insulin is based on a fixed number of Units of insulin.

46. An external infusion device according to claim 41, wherein the amount of time-shifted basal insulin is based on externally supplied values.

47. An external infusion device according to claim 46, wherein the externally supplied values include at least one of insulin action, insulin sensitivity, insulin-on-board, basal-on-board, anticipated carbohydrate intake, carbohydrate ratio, glycemic index values, blood glucose level, and target blood glucose value.

48. An external infusion device according to claim 41, wherein the amount of time-shifted basal insulin is based on a percentage of a user's current basal rate.

49. An external infusion device according to claim 48, wherein the user determines the percentage of the user's current basal rate.

50. An external infusion device according to claim 48, wherein the at least on processor recommends the percentage of the user's current basal rate.

51. An external infusion device according to claim 48, wherein the percentage of current basal rate is based on externally supplied values including at least one of insulin action, insulin sensitivity, insulin-on-board, basal-on-board, anticipated carbohydrate intake, carbohydrate ratio, glycemic index values, blood glucose level, and target blood glucose value.

52. An external infusion device according to claim 41, wherein the at least one processor determines the amount of time-shifted basal insulin based on blood glucose trends.

53. An external infusion device according to claim 52, wherein the blood glucose trends are supplied to the at least one processor by the user.

54. An external infusion device according to claim 52, wherein the blood glucose trends are downloaded to the external infusion device from a remote programmer.

55. An external infusion device according to claim 41, further including a glucose monitoring system to provide current blood glucose data to the at least one processor.

56. An external infusion device according to claim 55, wherein the external infusion device include a rate of change alarm to notify the user of changes in blood glucose levels.

57. An external infusion device according to claim 56, wherein the at least one processor recommends delivery of time-shifted basal insulin upon activation of the rate of change alarm.

58. An external infusion device according to claim 41, wherein the at least one processor includes at least one customizable bolus delivery profile.

59. An external infusion device according to claim 58, wherein the at least one customizable bolus delivery profile includes different percentages of at least one of a square wave bolus, a dual wave bolus, a normal bolus, a meal bolus, and a time-shifted basal insulin bolus.

60. An external infusion device according to claim 41, further including at least one alarm to provide alerts to the user.

61. An external infusion device according to claim 60, wherein the at least one alarm is used to remind the user to deliver time-shifted basal insulin.

62. An external infusion device according to claim 60, wherein the at least one alarm is used to remind the user to check blood glucose levels.

* * * * *